US012630450B1

(12) United States Patent
Darrag et al.

(10) Patent No.: US 12,630,450 B1
(45) Date of Patent: May 19, 2026

(54) SOMATIC EMBRYONIC CELL SUSPENSION FOR WASTEWATER TREATMENT

(71) Applicant: KING FAISAL UNIVERSITY, Hofouf (SA)

(72) Inventors: Hossam Moustafa Salem Darrag, Hofouf (SA); Emadaldeen Hamad M Hakami, Hofouf (SA)

(73) Assignee: KING FAISAL UNIVERSITY, Hofouf (SA)

( * ) Notice: Subject to any disclaimer, the term of this patent is extended or adjusted under 35 U.S.C. 154(b) by 0 days.

(21) Appl. No.: 19/352,687

(22) Filed: Oct. 8, 2025

(51) Int. Cl.
| | |
|---|---|
| *C02F 1/52* | (2023.01) |
| *C02F 1/50* | (2023.01) |
| *C12N 5/00* | (2006.01) |
| *C12N 5/04* | (2006.01) |
| *C02F 103/20* | (2006.01) |
| *C02F 103/32* | (2006.01) |

(52) U.S. Cl.
CPC .............. *C02F 1/5263* (2013.01); *C02F 1/50* (2013.01); *C12N 5/0025* (2013.01); *C12N 5/04* (2013.01); *C02F 2103/20* (2013.01); *C02F 2103/327* (2013.01); *C02F 2303/04* (2013.01)

(58) Field of Classification Search
CPC ...... C02F 1/5263; C02F 1/50; C02F 2103/20; C02F 2103/327; C02F 2303/04; C12N 5/0025; C12N 5/04
See application file for complete search history.

(56) References Cited

U.S. PATENT DOCUMENTS

| | | | | |
|---|---|---|---|---|
| 5,698,423 | A * | 12/1997 | Holowach-Keller | ......................... C12N 15/8243 435/244 |
| 7,943,049 | B1 * | 5/2011 | Alcantar | ............... C02F 1/5263 210/730 |
| 10,144,913 | B1 * | 12/2018 | Medina-Bolivar | ..... C12P 17/04 |
| 2016/0332899 | A1 | 11/2016 | Han | |
| 2018/0042194 | A1 * | 2/2018 | Gorr | ....................... A01H 4/002 |
| 2021/0386074 | A1 | 12/2021 | Mccarthy et al. | |

OTHER PUBLICATIONS

Nouhi et. al. "Comparative study of flocculation and adsorption behaviour of water treatment proteins from Moringa peregrina and Moringa oleifera seeds". Scientific Reports | 9:17945 | https://doi.org/10.1038/s41598-019-54069-2 (Year: 2019).*
Mustafa et. al. "Production of Benzyl Isothiocyanate from *Moringa peregrina* (Forssk.) Fiori via Suspension Cultures". Plant Tissue Cult. & Biotech. 33(2): 85-95 (Dec. 2023).*
Baldi et. al. "Fungal Elicitors for Enhanced Production of Secondary Metabolites in Plant Cell Suspension Cultures". A. Varma and A.C. Kharkwal (eds.), Symbiotic Fungi, Soil Biology 18, 373 DOI: 10.1007/978-3-540-95894-9_23, # Springer-Verlag Berlin Heidelberg (Year: 2009).*
Darrag et. al. "Exploring Ocimum basilicum's Secondary Metabolites: Inhibition and Molecular Docking against Rhynchophorus ferrugineus for Optimal Action". Plants 13, 491. https://doi.org/10.3390/plants13040491 (Year: 2024).*
Singh "Application of plant products in the synthesis and functionalisation of biopolymers" International Journal of Biological Macromolecules 237 124174 (Year: 2023).*
Pratibha Pandey, et al. "Combined Efficacy of Azadirachta Indica and Moringa Oleifera Leaves Extract as a Potential Coagulant in Ground Water Treatment"; Published online: Jun. 29, 2020; SN Applied Sciences.
Azmi Ahamd, et al. "Plant-Based Versus Metal-Based Coagulants in Aquaculture Wastewater Treatment: Effect of Mass Ratio and Settling Time"; Journal of Water Process Engineering; vol. 43; Oct. 2021.
Nigist Awish Hatiya,, et al. "Chemical Modification of Neem (*Azadirachta Indica*) Biomass as Bioadsorbent for Removal of PB2+ Ion From Aqueous Waste Water"; Adsorption Science & Technology; Published Nov. 3, 2022.
Franciele Pereira Camacho, et al. "The Use of Moringa Oleifera as a Natural Coagulant in Surface Water Treatment"; Chemical Engineering Journal; vol. 313, pp. 226-237; Apr. 1, 2017.
B.N.S. Murthy, et al. "Somatic Embryogenesis and Plant Regeneration of Neem (*Azadirachta indica A. juss.*)"; Plant Cell Reports; Published Apr. 1998.

* cited by examiner

*Primary Examiner* — Liam Royce
(74) *Attorney, Agent, or Firm* — Nath, Goldberg & Meyer; Joshua B. Goldberg

(57) ABSTRACT

A method of preparing at least once cell suspension product for treating wastewater, comprising germinating seeds from one or more plants selected from the group consisting of *M. peregrine, S. Potatorum, O. ficus-indica, O. basilicum,* and *H. tuberculatum* to provide plant sprouts; cutting the sprouts to provide plant parts; adding the plant parts to a culture medium; adding a basal medium to the culture medium to initiate development of the cell suspension; maintaining the cell suspension for a period of time to harvest callus in the cell suspension; and isolating at least one cell suspension product from the cell suspension.

10 Claims, 3 Drawing Sheets

SOMATIC EMBRYONIC CELL SUSPENSION FOR WASTEWATER TREATMENT

BACKGROUND OF THE INVENTION

Field of the Invention

The disclosure of the present patent application relates to water treatment solutions and, particularly, to a somatic embryonic cell suspension for wastewater treatment.

Description of Related Art

Wastewater treatment plants are facilities designed to clean sewage and wastewater before returning it to the environment. They utilize various processes, including: physical, chemical, and biological methods to purify water, in preliminary, primary, secondary, and tertiary stages. Types of wastewater treatment plants include Conventional Activated Sludge Plants, Sequencing Batch Reactors, Membrane Bioreactors, and more.

The wastewater treatment process involves removing solids and pollutants, breaking down organic matter, and restoring oxygen content in the water. These wastewater treatment plants play a crucial role in maintaining environmental health by ensuring that treated water is safe for discharge back into natural water bodies.

Agricultural wastewater treatment is a farm management agenda for controlling pollution from confined animal operations and from surface runoff that may be contaminated by chemicals in fertilizer, pesticides, animal slurry, crop residues or irrigation water. Agricultural wastewater treatment is required for continuous confined animal operations like milk and egg production. It may be performed in plants using mechanized treatment units similar to those used for industrial wastewater. Where land is available for ponds, settling basins and facultative lagoons may have lower operational costs for seasonal use conditions from breeding or harvest cycles. Animal slurries are usually treated by containment in anaerobic lagoons before disposal by spray or trickle application to grassland. Constructed wetlands are sometimes used to facilitate treatment of animal wastes.

Nonpoint source pollution includes sediment runoff, nutrient runoff and pesticides. Point source pollution includes animal wastes, silage liquor, milking parlour (dairy farming) wastes, slaughtering waste, vegetable washing water and firewater. Many farms generate nonpoint source pollution from surface runoff which is not controlled through a treatment plant.

Thus, new kinds of water treatment chemicals that are simple and inexpensive to produce are desirable.

SUMMARY OF THE INVENTION

The present disclosure relates to using a cell suspension formed from plant somatic embryogenesis in the production of at least once cell suspension product including polyphenols and protein. The at least one cell suspension product may be used for treating wastewater, including sewage, agricultural and industrial water (waste of animal, food industries, dairy factories and milking parlors.

A method of preparing at least once cell suspension product for treating wastewater, comprising germinating seeds from one or more plants selected from the group consisting of *M. peregrine, S. Potatorum, O. ficus-indica, O. basilicum*, and *H. tuberculatum* to provide plant sprouts;

cutting the sprouts to provide plant parts; adding the plant parts to a culture medium; adding a basal medium to the culture medium to initiate development of the cell suspension; maintaining the cell suspension for a period of time to harvest callus in the cell suspension; and isolating at least one cell suspension product from the cell suspension.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Definitions

Figure 1:
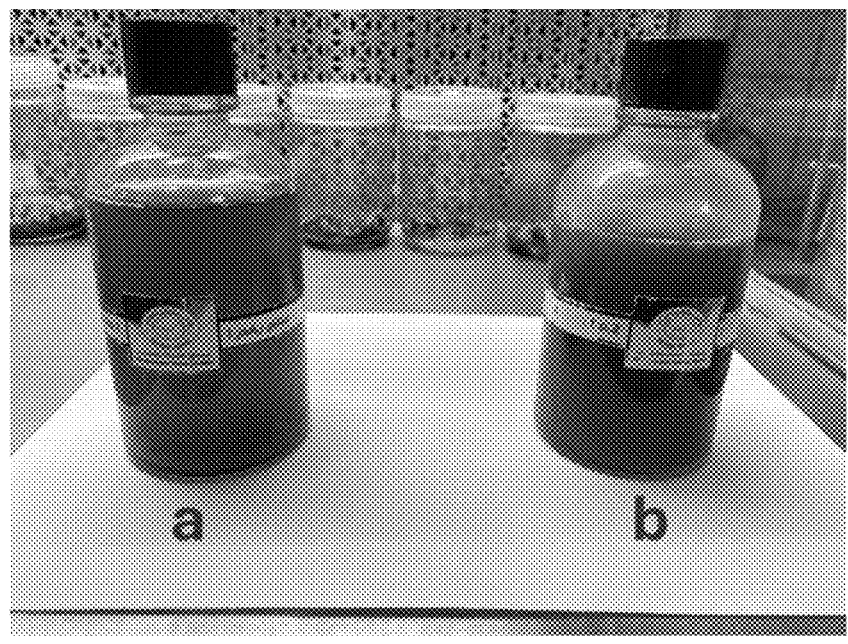
FIG. 1 illustrates an embodiment of a product 1 (a) and product 2 (a).

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present disclosure relates to the use of a cell suspension formed when somatic embryogenesis is conducted. At least one cell suspension product can be isolated from the cell suspension and used for treating wastewater, such as sewage, waste agricultural water, and waste industrial waters. The at least one cell suspension product can include one or more secondary metabolites, such as polyphenols and protein. In an embodiment, the at least one cell suspension product comprises a first cell suspension product. In an embodiment, the first cell suspension product comprises secondary metabolites isolated from the cell suspension. In one embodiment, the at least one cell suspension product comprises a second cell suspension product. In an embodiment, the second cell suspension product comprises a cell suspension extract, e.g., a water extract, isolated from the cell suspension. At least one cell suspension product can be dispersed in wastewater for purifying or treating the wastewater. In an embodiment, both the first cell suspension product and the second cell suspension product can be dispersed in the wastewater for purifying or treating the wastewater. In an embodiment, the wastewater can include animal waste and/or waste obtained from food industries, dairy factories and milking parlors. In an embodiment, treating the wastewater with the cell suspension extract and/or cell suspension product can result in removal of or a reduced concentration of *E. coli, Bacillus subtilis*, and fecal coliforms in the wastewater.

According to an embodiment, more than one cell suspension can be formed using different plant seeds and the at least one cell suspension products of different cell suspensions can be used in combination to treat wastewater. For example, the first cell suspension product can be obtained from a first cell suspension and a second cell suspension product can be obtained from a second cell suspension. In an embodiment, the first cell suspension can be derived from seeds of at least one plant selected from the group consisting of *M. peregrine, S. Potatorum, O. ficus indica, A. indica, O. basilicum*, and *H. tuberculatum* and the second cell suspension can be derived seeds of a plant selected from the group consisting of *M. peregrine* and *A. ficus-indicia*.

Somatic embryogenesis is an artificial process in which a plant or embryo is derived from a single somatic cell. Somatic embryos are formed from plant cells that are not normally involved in the development of embryos, i.e., ordinary plant tissue. No endosperm or seed coat is formed around a somatic embryo.

For somatic embryogenesis, cells derived from a competent source tissue are cultured to form an undifferentiated mass of cells called a callus. Plant growth regulators in the tissue culture medium can be manipulated to induce callus formation and subsequently changed to induce embryos to form the callus. The ratio of different plant growth regulators required to induce callus or embryo formation varies with the type of plant.

As set forth in the present disclosure, calluses can be formed in the cell suspensions including somatic embryonic cells derived from one or more plants selected from the group consisting of *Arabica Moringa* (*Moringa peregrine* Forssk.), *Nirmali* (clearing-nut tree) (*Strychnos Potatorum* Linn.), *Cactus* (*Opuntia ficus indica* Shamiya.), neem (*Azadirachta indica* A.Juss.), Hasawi basil (*Ocmium basilicum*), and *Haplophyllum tuberculatum* (Forssk.). Once the calluses are formed, at one cell suspension product can be isolated from the cell suspension which can provide affordable, simple, and environmentally friendly natural bio-wastewater treatment products.

The cell suspension described herein may be used for developing and producing active secondary metabolite compounds at concentrations ranging from 8-10 times higher than those naturally present in plants.

As described herein, the cell suspensions can be formed when one or more plants selected from the group consisting of *Arabica moringa* (*Moringa peregrine* Forssk.), *Nirmali* (clearing-nut tree) (*Strychnos Potatorum* Linn.), *Cactus* (*Opuntia ficus-indica* Shamiya.), neem (*Azadirachta indica* A.Juss.), Hasawi basil (*Ocmium basilicum*), and *Haplophyllum tuberculatum* (Forssk.) are grown in a culture medium.

According to an embodiment, the at least one cell suspension product can include one or more compounds derived from a cell suspension in which somatic embryogenesis has occurred or from which callus is harvested. In an embodiment, seeds of one or more of *Moringa peregrina* (*M. peregrine*), *Strychnos potatorum, Opuntia ficus-indica, Azadirachta indica, Ocmium basilicum*, and *Haplophyllum tuberculatum* are individually added to separate culture media to harvest callus. In an embodiment, once the callus are harvested, the resulting friable callus tissue is transferred into fresh liquid media to establish the cell suspension. A first cell suspension product can be derived from the cell suspension by isolating secondary metabolites in the cell suspension. In an embodiment, a second cell suspension product, such as a water extract, can be derived from the cell suspension. The first cell suspension product and the second cell suspension product (also referred to herein as a cell suspension extract) may include secondary metabolites, such as polyphenols and proteins.

FIG. 1 illustrates a bottle including the cell suspension product (a) and a bottle of the cell suspension extract (b). The cell suspension product has an orange-brownish color and is translucent. The second cell suspension product has a greenish color and is more opaque. In some embodiments, a concentration of the polyphenols and the proteins in the cell suspension product is at least about 8 times to at least about 10 times, at least 8 times to 10 times, and about 8 times to 10 times greater than concentrations in natural plant tissues.

Figure 2:
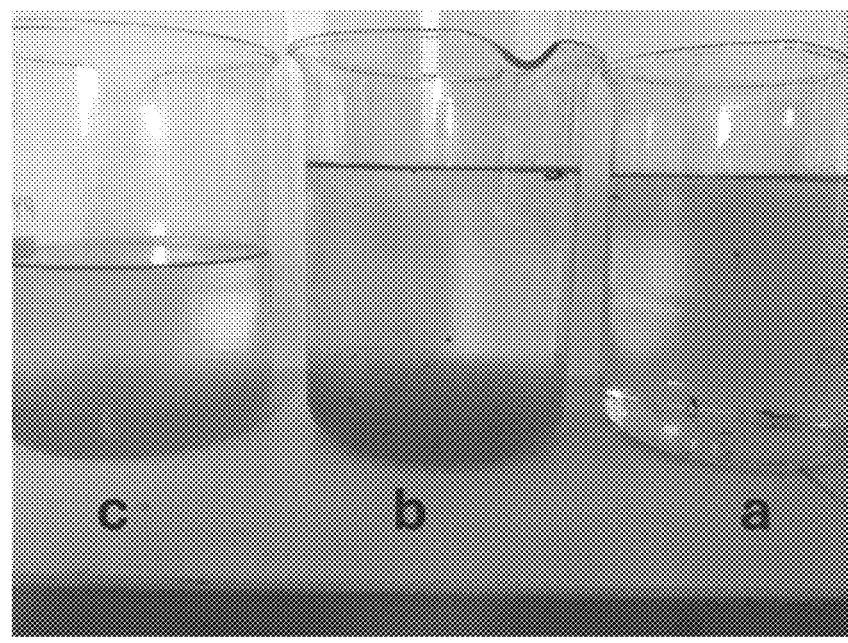
FIG. 2 illustrates wastewater treatment stages: (a) mixture of wastewater; (b) wastewater treated with products; (c) sediment layer after treatment.

According to an embodiment, the present disclosure relates to a method of treating wastewater using at least one cell suspension product. In various embodiments, the method may include adding an amount of the first cell suspension product to the wastewater to be treating and then adding an amount of the second cell suspension product to the wastewater to be treated, and leaving the cell suspension in the wastewater for at least about 1 minute to at least about 3 minutes, at least 1 minute to at least 3 minutes, or about 1 minute to about 3 minutes. In other embodiments, the amount added is proportional to the amount of wastewater being treated, such as by non-limiting example, a couple of drops of each of the first product and the second product is added to a 500 mL standard laboratory beaker as illustrated in FIG. 2. In some embodiments, the method of treating wastewater includes adding about 1 mg/L of the first cell suspension product to the wastewater. In some embodiments, the method of treating wastewater includes adding between about 3 mg/L and about 5 mg/L of the second cell suspension product to the wastewater.

In various embodiments of the method of treating wastewater, *E. coli, Bacillus subtilis*, and fecal coliforms may be removed from the treated wastewater.

In other embodiments of the method of treating wastewater, concentrations of *E. coli*, the *Bacillus subtilis*, and the fecal coliforms may be reduced to 0 cfu/100 mL after treating the wastewater with the one or more cell suspension products and/or cell suspension extracts described herein.

In another embodiment of the method of treating wastewater, a percentage of about 99.6% to about 99.87% of total suspended solids may be removed from the treated wastewater upon treating the wastewater with the cell suspension product and/or the cell suspension extract.

In still other embodiments of the method of treating wastewater, 100% of fecal coliforms may be eliminated from the wastewater upon treating the wastewater with the cell suspension product and/or the cell suspension extract.

The present disclosure also relates to a method of forming cell suspension and obtaining a cell suspension product therefrom. The method may include, delinting and sterilizing seeds of one or more plants selected from the group consisting of *M. peregrine, S. Potatorum, A. ficus-indica*, and *O. basilicum*; germinating the seeds (with sterile blotting paper) to produce plant sprouts, and cutting the sprout to provide plant parts e.g., hypocotyls, epicotyl, and cotyledonary. In various embodiments, the seeds may be germinated with sterile blotting paper. In some embodiments, the seeds may be germinated for at least about 3 to at least about 5 days, at least 3 days to at least 5 days, and about 3 days to about 5 days. After cutting, the plant parts can be added to a culture medium. In an embodiment, the hypocotyls, epicotyl, and cotyledonary of *M. peregrine, S. Potatorum, O. ficus-indica, O. basilicum*, a piece of leaf from *O. ficus-indica*, and a piece of leaf from *H. tuberculatum* can be added to the culture medium.

In various embodiments, the culture medium is Murashige and Skoog medium (MS medium). In an embodiment, plant growth regulators (PGRs) can be added to the culture medium. In an embodiment, the PGRs can include kinetin, indole-3-butyric acid (IBA) 2,4-D (2,4-dichlorophenoxyacetic acid), and NAA (naphthaleneacetic acid).

In an embodiment, *Verticillium dahlia*, and *Arbuscular mycorrhizal* can be added to the Abiotic *Verticillium dahlia*, and *Arbuscular mycorrhizal* fungi has been extensively utilized to boost secondary metabolite production. In recent times, there has been a resurgence of interest in the use of cell suspension cultures for the generation of secondary metabolites from *O. basilicum* (in vitro).

Figure 3:
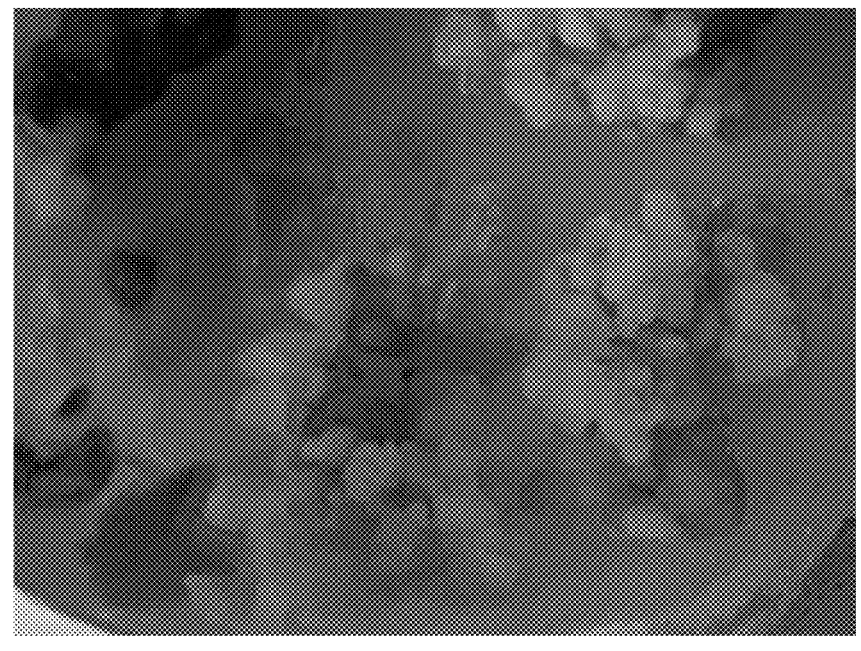
FIG. 3 illustrates initiation of cell suspension of *Moringa peregrine* Forssk.
Figure 4:
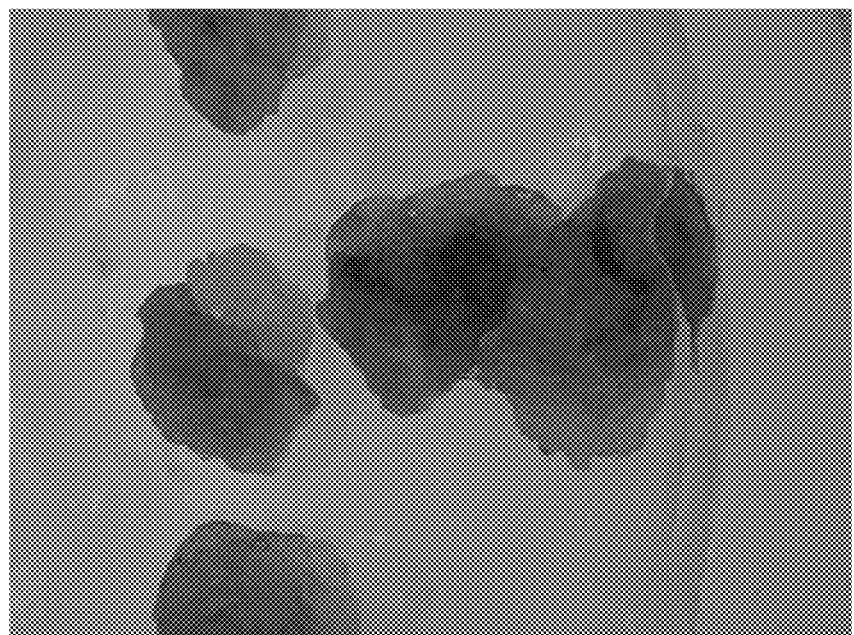
FIG. 4 illustrates initiation of cell suspension of *Strychnos Potatorum* Linn.
Figure 5:
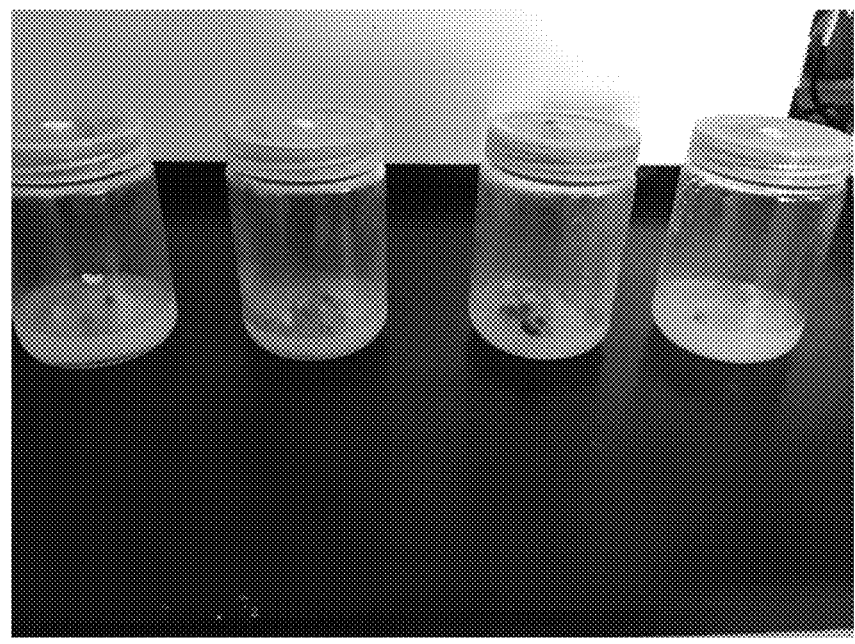
FIG. 5 illustrates callus initiation of *Opuntia ficus-indica* Shamiya, *Azadirachta indica* A.Juss, *Ocmium basilicum*, and *Haplophyllum tuberculatum* (Forssk.) A.Juss.

The method includes initiating development of the cell suspension, e.g., with Linsmaier & Skoog (LS) Basal Medium, to harvest callus. In various embodiments, a maximum callus concentration can be harvested in a period of about 40 days to about 45 days. Referring to FIGS. 3 and 4, initiation of cell suspension from *Moringa peregrine* Forssk and *Strychnos Potatorum* Linn, is illustrated, respectively.

In an embodiment, the callus can be harvested from the cuttings of plant parts of *M. peregrine, S. Potatorum, A. ficus-indica, O. basilicum, O. ficus-indica*, and *H. tuberculatum*. Referring to FIG. 7, callus initiation of *Opuntia ficus-indica* Shamiya, *Azadirachta indica* A.Juss, *Ocmium basilicum*, and *Haplophyllum tuberculatum* (Forssk.) A.Jussi, is illustrated.

In various embodiments, the method further includes extracting samples from the cell suspension; drying the samples using anhydrous $Na_2SO_4$; and forming the first cell suspension product.

In some embodiments, the extracting the samples from the cell suspension includes using methanol and agitation for at least about 12 hours.

In other embodiments, cell suspension products obtained from media in which *M. peregrine, S. Potatorum, O. ficus indica, A. indica, O. basilicum*, and *H. tuberculatum* were grown are combined in proportions of about 3 ml, about 2 ml, about 1 ml, about 1 ml, about 1 ml, and about 1 ml, respectively, and added to the culture medium.

In another embodiment, the method further includes obtaining a water extract from a cell suspension derived from plant parts of *M. peregrine* and *A. ficus-indica* by adding NaCl to a sample obtained from the cell suspension to form a mixture; agitating the mixture to form the water extract. The proportions of *M. peregrine* and *A. ficus-indica* plant parts may be 1:1.

The principles described may be further described using various examples.

EXAMPLES

Example 1

Preparing Cell Suspension

The seeds of *M. peregrine, S. Potatorum, A. ficus-indica*, and *O. basilicum* underwent delinting, sterilization, and subsequent germination in Petri plates with sterile blotting paper. After a period of three to five days, the plant parts (specifically hypocotyls, epicotyl, and cotyledonary) of *M.*

*peregrine, S. Potatorum, O. ficus-indica, O. basilicum*, and also a piece 30 of a 2×2 cm leaf from the *O. ficus-indica, H. tuberculatum* plant were introduced into a culture medium known as MS medium.

The solid medium was enhanced with plant growth regulators (PGRs) at concentrations of 0.5 mg/L for 2,4-D, kinetin, and 33 Naphthaleneacetic acid (NAA), and 1 mg/L for Indole-3-butyric acid (IBA), which demonstrated that the MS medium containing 3% sucrose with 6.0 g/L of agar was the most efficient way to induce callus in a mixture including *M. peregrine, S. potatorum, A. ficus-indica*, and *O. basilicum* plant parts.

Hormonal supplementation with serial concentrations of 0.3 mg/L kinetin, 0.3 mg/L 2,4-D, 0.2 mg/L NAA, and 1 mg/L of IBA were added to the medium to confirm the relative callus weights of *O. ficus-indica* and *H. tuberculatum* cultivated under ideal circumstances, both with and without the abiotic activator *V. dahlia* and *A. mycorrhizal*.

Initiation of the cell suspension was conducted using Linsmaier & Skoog (LS) Basal Medium, a liquid medium, over a duration of 40-45 days. After 38-45 days of development, maximum callus was harvested in the cell suspension, and the mean cell weight, total phenolic, flavonoids, condensed tannins, and total proteins increased progressively afterward in the cell suspension.

Example 2

Preparation of Product 1

Compounds (first cell suspension product) were extracted from the cell suspension using methanol (ratio cell:methanol 1:9) via agitation for a duration of 12 hours and then dried using anhydrous $Na_2SO_4$ to form the first cell suspension product (product No. 1). A mixture of *M. peregrine, S. Potatorum, O. ficus indica, A. indica, O. basilicum*, and *H. tuberculatum* was made in according to the proportions 3, 2, 1, 1, 1, and 1, respectively to form product No. 1.

Example 3

Preparation of Product 2

The water extract of *M. peregrine*, and *A. ficus-indica* (second cell suspension product) was prepared by mixing the cell suspension derived from *M. peregrine*, and *A. ficus-indica* plant parts with NaCl (0.1M) via agitation for a duration of 3-4 hours to form the second cell suspension product (product No. 2). The water extract of *M. peregrine*, and *Opuntia ficus-indica* was prepared by combining the cell suspension derived extracts from both species in equal proportions (1:1 ratio), to form product No. 2. The chemical contents of cell suspension extract from each plant species were analyzed using LC/MS-MS. (See Table 1) The results represent the mean values and standard deviations (SD) from three separate experiments (n=3). For fragment ions, average relative abundances are indicated in parentheses. Retention time is referred to as RT. When a negative molecular ion was detected, it is noted with "[M-H]" and the corresponding m/z (mass-to-charge ratio). Retention indices were determined relative to standards, with the MS library value (Wiley) and the experimental retention index (exp RI) from NIST also provided.

TABLE 1

| LC-MS Data for *Moringa peregrine* Forssk cell suspensions extract | | | | | |
|---|---|---|---|---|---|
| Retention Time (RT) (min) | Tentative Compounds | Formula | [M − H]⁻ (m/z) | ESI +/− | Fragmentation ions (m/z) |
| 2.920 | Caffeoyl-glucoside | $C_{15}H_{18}O_9$ | 341.087 | − | 179, 135 |
| 4.009 | Pyrogallol | C6H6O3 | 127.0387 | + /− | 127 |
| 4.090 | Hydroxytyrosol acetate | C10H12O4 | 195.157 | − | 153, 135, 97, 80 |
| 4.136 | Hesperidin | C28H34O15 | 609.1855 | − | 301 |
| 4.501 | 6''-O-Malonylglycitin | C25H24O13 | 533.1297 | + | 533 |
| 4.551 | Rosmanol | C20H26O5 | 345.1693 | − | 301 |
| 6.216 | Gallic acid | C7H6O5 | 171.0298 | − | 125 |
| 6.302 | 3-Sinapoylquinic acid | C18H22O10 | 399.1279 | + | 223, 191 |
| 6.302 | Cinnamoyl glucose | C15H18O7 | 311.1133 | + | 147, 131, 103 |
| 6.905 | Piceatannol | C14H12O4 | 243.0671 | − | 225, 201, 174, 159 |
| 9.737 | 3'-Hydroxy-3,4,5,4'-tetramethoxystilbene | C17H18O5 | 303.1225 | + | 285 |
| 10.718 | Protocatechuic acid | C7H6O4 | 155.0341 | + | 109 |
| 10.34 | Glucomoringin | C17H25NO13S | 570.157 | − | 328, 275, 97 |
| 10.870 | 3-Caffeoylquinic glycoside | C25H24O13 | 515.129 | − | 353, 341, 179, 135 |
| 13.038 | 3-Caffeoylquinic acid | C16H18O9 | 353.0879 | − | 253, 190, 144 |
| 13.170 | Rosmarinic acid | C18H16O8 | 359.0769 | − | 197, 179, 161, 135 |
| 13.549 | Protocatechuic acid 4-O-glucoside | C13H16O9 | 315.0725 | − | 153 |
| 13.720 | Caffeic acid 4-O-glucuronide | C15H16O10 | 355.0684 | − | 179, 161 |
| 14.024 | Quercetin-di-O-glycoside | C27H30O16 | 625.158 | − | 463, 301 |
| 14.151 | Neoeriocitrin | C27H32O15 | 595.1659 | − | 459, 287, 151 |
| 14.188 | Scopoletin | C10H8O4 | 191.0343 | − | 175, 147 |
| 14.203 | Medioresinol | C21H24O7 | 389.1595 | + | 389.1595 |
| 15.587 | Rhoifolin | C27H30O14 | 577.1583 | − | 431, 269 |
| 15.929 | Vitexin | C21H20O10 | 431.098 | − | 341, 311, 283 |
| 15.982 | p-Hydroxybenzoic acid | C7H6O3 | 137.0252 | − | 93 |
| 17.002 | (+)-Gallocatechin | C15H14O7 | 305.0673 | − | 269, 219 |
| 18.156 | Lariciresinol-sesquilignan | C30H36O10 | 555.2220 | − | 359 |
| 18.203 | Caffeic acid | C9H8O4 | 179.0349 | − | 143, 135, 133 |
| 18.203 | p-Anisaldehyde | C8H8O2 | 135.0451 | − | 107, 93, 79 |
| 18.341 | 3-Feruloylquinic acid | C17H20O9 | 367.1035 | − | 298, 288, 192, 191 |
| 18.697 | 3-p-Coumaroylquinic acid | C16H18O8 | 337.0926 | − | 265, 173, 162 |
| 19.885 | Secoisolariciresinol-sesquilignan | C30H38O10 | 557.2390 | − | 539, 521, 509, 361 |
| 20.214 | Naringin | C27H32O14 | 579.1739 | − | 271 |
| 20.611 | Coumarin | C9H6O2 | 145.0293 | − | 101 |
| 21.174 | Procyanidin B2 | C30H26O12 | 577.1354 | − | 451, 425, 289 |

TABLE 1-continued

| Retention Time (RT) (min) | Tentative Compounds | Formula | [M – H]⁻ (m/z) | ESI +/− | Fragmentation ions (m/z) |
|---|---|---|---|---|---|
| 21.174 | Apigenin 6-C-glucoside | C21H20O10 | 431.1002 | − | 269 |
| 21.683 | Myricetin 3-O-rhamnoside | C21H20O12 | 463.0872 | − | 317 |
| 22.054 | Apigenin-6,8-di-C-glycopyranoside | C27H30O15 | 593.151 | − | 503, 473, 383, 353 |
| 22.814 | (−)-Epigallocatechin 7-O-glucuronide | C21H22O13 | 483.1133 | + | 483 |
| 23.010 | 6″-O-Malonylgenistin | C24H22O13 | 517.1013 | − | 271 |
| 23.007 | Quercetin-3-O-rutinoside (Rutin) | C27H30O16 | 609.146 | − | 463, 301, 179 |
| 23.081 | Quercetin-3-O-glycoside | C21H20O12 | 463.087 | − | 301, 271, 179 |
| 23.085 | Ferulic acid | C10H10O4 | 193.0502 | − | 178, 149, 134 |
| 23.438 | Procyanidin trimer C1 | C45H38O18 | 865.2009 | − | 739, 695, 577, 451 |
| 24.095 | p-Coumaric acid 4-O-glucoside | C15H18O8 | 325.0936 | − | 163, 119 |
| 46.510 | Quercetin- hydroxymethylglutaroyl glycoside | C28H24O15 | 607.165 | − | 505, 463, 301, 179 |
| 47.010 | Quercetin-3-O-acetyl-glycoside | C23H20O13 | 505.092 | − | 463, 301, 271, 179 |
| 24.378 | Diosmin | C28H32O15 | 607.1651 | − | 301, 300 |
| 24.681 | p-Coumaroyl tartaric acid | C13H12O8 | 295.0471 | − | 115 |
| 24.681 | (−)-Epigallocatechin 3-O-gallate | C22H18O11 | 457.0780 | − | 305, 169 |
| 24.972 | Kaempferol-3-O-glycoside | C21H20O11 | 447.093 | − | 285, 255 |
| 26.216 | Naringenin 7-O-glucoside | C21H22O10 | 435.1290 | + | 273 |
| 26.707 | Dihydroformononetin | C16H14O4 | 271.0968 | + | 253, 137 |
| 26.724 | Quercetin | C15H12O7 | 301.035 | − | 179, 151 |
| 26.759 | Cinnamic acid | C9H8O2 | 147.0450 | − | 129, 103 |
| 26.806 | Esculin | C15H16O9 | 339.0705 | − | 177 |
| 26.949 | Umbelliferone | C9H6O3 | 161.0247 | − | 133 |
| 28.604 | 3,4′,7-Tetrahydroxyflavone | C15H10O6 | 287.0555 | + | 287 |
| 29.106 | p-Coumaric acid | C9H8O3 | 163.0402 | − | 119 |
| 30.894 | 3,7-Dimethylquercetin | C17H14O7 | 329.0680 | − | 314, 299, 271 |
| 33.081 | 3,5-Diferuloylquinic acid | C27H28O12 | 543.1492 | − | 193, 191, 134 |
| 36.425 | 1,2,2′-Triferuloylgentiobiose | C42H46O20 | 871.2618 | + | 676, 195, 177 |
| 38.744 | Carvacrol | C10H14O | 151.1121 | + | 107 |
| 39.642 | Kaempferol | C15H12O6 | 285.040 | − | 255, 179 |
| 42.621 | Mellein | C10H10O3 | 177.0553 | − | 133 |
| 43.624 | Lariciresinol | C20H24O6 | 359.1504 | − | 329, 192, 178, 175, 160 |
| 45.726 | Matairesinol | C20H22O6 | 357.1345 | − | 313, 342, 151, 136 |
| 45.735 | Kaempferol-O-acetyl-glycoside | C23H20O12 | 489.104 | − | 285, 255 |
| 45.793 | Isorhamnetin-O-acyl-glycoside | C24H22O12 | 519.118 | − | 421, 315, 285 |
| 45.817 | Carnosic acid | C20H28O4 | 331.1920 | − | 287 |
| 49.606 | Hydroxytyrosol 4-O-glucoside | C14H20O8 | 315.1097 | − | 153, 123 |
| 50.044 | Carnosol | C20H26O4 | 329.1766 | − | 285 |
| 54.991 | Glycitein 7-O-glucuronide | C22H20O11 | 459.0916 | − | 441, 283, 267 |
| 55.134 | Equol 7-O-glucuronide | C21H22O9 | 417.1184 | − | 241 |
| 62.904 | Rosmadial | C20H24O5 | 343.1556 | − | 299 |

Example 4

Treating Wastewater

The cell suspension products derived from somatic embryogenesis described above was used for wastewater treatment (sewage, agricultural drainage water, drainage of cow and sheep pens, food industries, dairy factories and milking parlors). The wastewater was collected from Research & Training Station, Livestock Department, King Faisal University. The first and second cell suspension products were introduced to the wastewater (FIG. 2a) and produced coagulated flocculant (FIG. 2b), and separate solids waste (FIG. 2c) using concentrations not exceeding 2-5 mL/m³ (cell suspension product in wastewater). The wastewater mixture was treated for 1 to 3 minutes according to the contents of waste. The turbidity (NTU), biochemical oxygen demand (BOD), chemical oxygen demand (COD), total suspended solids (TSS), total solids (TS) values, and hazardous metals such as Pb, Cu, Cd, and Zn were measured before and after treatment for each wastewater sample. As presented in Table 2, the NTU (92.74-94.32%), COD (92.04-93.68%), TSS (99.6-99.87%), Pb 56 (100%), Cu (97.26-97.54%), Cd (92.98-93.84%), and Zn (92.14-92.67%) were found to have the highest removal rates according to the wastewater types, and NTU, BOD, TS, and TSS values equal 3.4, 0, 24-124, 13-67 mg/L, respectively.

TABLE 2

| Concentrations and Values of Different Wastewater Parameters Before and After Treatment with Product No. 1 and Product No. 2 for Each Plant Extract | | | |
|---|---|---|---|
| Parameter | Concentration of wastewater | Concentration after treatment | Removal rate |
| Turbidity (NTU) | 315.32 | 3.4 | 92.74% |
| total suspended solids (TSS) | 1294.8-6691.29 | 13-67 | 99.6-99.87% |
| total solids (TS) | 712-2014 | 24-124 | 96.63-93.84% |
| biochemical oxygen demand (BOD5) | 641 | 0 | 100% |
| chemical oxygen demand (COD) | 1625 | 127 | 92.04-93.68% |

TABLE 2-continued

Concentrations and Values of Different Wastewater Parameters Before and
After Treatment with Product No. 1 and Product No. 2 for Each Plant Extract

| Parameter | Concentration of wastewater | Concentration after treatment | Removal rate |
|---|---|---|---|
| Cadmium | 0.5 | 0.0046-0.00469 | 92.98-93.84% |
| Lead | 5 | 0.01 | 100% |
| Copper | 10 | 0.097 | 97.26-97.54% |
| Zinc | 100 | 0.92 | 92.14-92.67% |
| *Escherichia coli* | 780 | 0 | 100% |
| Total coliform (TC) | 573 | 0 | 100% |
| Fecal streptococci (FS) | 434 | 0 | 100% |
| Fecal coliform (FC) | 517 | 0 | 100% |

Pathogens *Escherichia coli* and *Bacillus subtilis* and *Candida albicans* were detected in wastewaters, and total coliform (TC) and the fecal streptococci (FS), fecal coliform (FC) were calculated. Treatment of the wastewater with wastewater treatment products No. 1 and No. 2 removed *E. coli* and *B. subtilis* and *C. albicans* from the wastewater. The TC, FC, and FS in treated wastewater equaled zero (0 cfu/100 mL). The first product (No. 1) and second product (No. 2) were effective against larvae of mosquito in wastewater. The cost of treatment for each cubic meter (m³) of wastewaters equal $ 0.008-0.012 (USD) compared with traditional methods costs (*Moringa stenopetala* powder $0.042, Chitosan $0.025, and *Azadirachta indica* A. Juss $0.56).

These results suggest large-scale generation of the secondary metabolites (polyphenols, and proteins) may be achieved using the straightforward and environmentally friendly cell suspension described herein. These methods may be used in the cultivation of vegetables and fruits directly. The secondary metabolites are free of any pathogens. Preparation of products No. 1 and No. 2, is relatively simple and cost-effective. These methods may also open the way to increase the production of compounds in the laboratory in large quantities at a low cost using large bioreactors.

It is to be understood that the cell suspension products and water treatment methods described herein are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A method of preparing at least one cell suspension product for treating wastewater, comprising:

germinating seeds from one or more plants selected from the group consisting of *Moringa peregrina, Strychnos Potatorum, Opuntia ficus, Azadirachta indica, Ocmium basilicum,* and *Haplophyllum tuberculatum* to provide plant sprouts;

cutting the sprouts to provide plant parts;

adding the plant parts to a culture medium;

adding a basal medium to the culture medium to initiate development of the cell suspension;

maintaining the cell suspension for a period of time to harvest callus in the cell suspension; and isolating at least one cell suspension product from the cell suspension;

wherein the at least one cell suspension product includes one or more secondary metabolites, the one or more secondary metabolites comprising polyphenols and proteins.

2. The method of claim 1, wherein the plant parts comprise one or more plant parts selected from the group consisting of hypocotyls, epicotyl, cotyledonary, and leaves.

3. The method of claim 1, wherein the culture medium is Murashige and Skoog medium.

4. The method of claim 1, further comprising adding one or more plant growth regulators to the culture medium.

5. The method of claim 4, wherein the one or more plant growth regulators is selected from the group consisting of kinetin, indole-3-butyric acid (IBA) 2,4-D (2,4-dichlorophenoxyacetic acid), and NAA (naphthaleneacetic acid).

6. The method of claim 1, further comprising adding *Verticillium dahlia*, and *Arbuscular mycorrhizal* to the culture medium.

7. The method of claim 1, wherein the at least one cell suspension product comprises the first cell suspension product and a second cell suspension product, the second cell suspension product being a water extract of the first cell suspension.

8. A method of treating wastewater, comprising adding the first and second cell suspension products of claim 7 in the wastewater.

9. The method of claim 1 further comprising obtaining a second cell suspension product from a second cell suspension derived from seeds of *Moringa peregrina* and *Opuntia ficus indica*; and wherein the at least one cell suspension product comprises a first cell suspension product and the second cell suspension product.

10. A method of treating wastewater, comprising adding the first cell suspension product and the second cell suspension product of claim 9 to the wastewater.

*    *    *    *    *